(12) United States Patent
Glockler

(10) Patent No.: US 6,251,101 B1  
(45) Date of Patent: Jun. 26, 2001

(54) SURGICAL LASER SYSTEM MICROSCOPE WITH SEPARATED OCULAR AND OBJECTIVE LENSES

(75) Inventor: Herrmann J. Glockler, Cupertino, CA (US)

(73) Assignee: VISX, Incorporated, Santa Clara, CA (US)

(*) Notice: Subject to any disclaimer, the term of this patent is extended or adjusted under 35 U.S.C. 154(b) by 0 days.

(21) Appl. No.: 09/105,073

(22) Filed: Jun. 26, 1998

(51) Int. Cl.⁷ ...................................................... A61F 9/008
(52) U.S. Cl. .................................. 606/5; 606/10; 606/13; 359/368; 359/372
(58) Field of Search ........................... 606/2, 3–6, 10–13, 606/19; 359/368, 372, 379–382

(56) References Cited

U.S. PATENT DOCUMENTS

| | | |
|---|---|---|
| 4,665,913 | 5/1987 | L'Esperance, Jr. . |
| 4,911,711 | 3/1990 | Telfair et al. ............................. 605/5 |
| 4,998,810 | 3/1991 | Sander et al. ........................ 350/528 |
| 5,022,743 | 6/1991 | Kino et al. ............................. 350/507 |
| 5,219,344 | 6/1993 | Yoder, Jr. ................................. 605/5 |
| 5,296,963 | 3/1994 | Murakami et al. .................. 359/389 |
| 5,303,082 | 4/1994 | Obuchi et al. ....................... 359/371 |
| 5,323,009 | 6/1994 | Harris ................................ 250/458.1 |
| 5,382,770 | 1/1995 | Black et al. .................... 219/121.63 |
| 5,442,487 | 8/1995 | Mizuno . |
| 5,506,725 | 4/1996 | Koike et al. ......................... 359/388 |
| 5,539,572 | 7/1996 | Greenberg et al. ................. 359/368 |
| 5,556,395 | 9/1996 | Shimmick et al. ...................... 606/4 |
| 5,585,964 | * 12/1996 | Schalz ................................... 359/368 |
| 5,636,058 | 6/1997 | Amemiya ............................. 359/656 |
| 5,646,791 | 7/1997 | Glockler ............................... 359/831 |
| 5,683,379 | 11/1997 | Hohla ....................................... 606/5 |
| 5,713,892 | 2/1998 | Shimmick ................................ 606/5 |

FOREIGN PATENT DOCUMENTS

| | | |
|---|---|---|
| 3221804 A1 | 12/1983 | (DE) . |
| 2 122 045 | 1/1984 | (GB) . |
| 2 231 681 | 11/1990 | (GB) . |
| 6-18786 | 1/1994 | (JP) . |

OTHER PUBLICATIONS

O.A. Schaedlich, "Microprinter for Wafer or Chip Identification", IBM Technical Disclosure Bulletin, vol. 15, No. 8, Jan. 1973, pp. 2554–2555.

* cited by examiner

*Primary Examiner*—David M. Shay  
(74) *Attorney, Agent, or Firm*—Townsend Townsend & Crew LLP; Mark D. Barrish, Esq.

(57) ABSTRACT

The invention provides improved structures, systems, and methods for supporting the optical elements of a microscope relative to the optical train of a laser surgery system. As the field of view of the microscope is substantially fully determined by the position of the objective lens, the laser delivery optics and the microscope can be aligned with a target location of the patient's eye by accurately aligning just the objective lens with the delivery optics. By structurally separating the objective lens from the other optical components of the microscope, and by maintaining accurate alignment between the objective lens and the laser delivery optics with a simple, tight-tolerance support structure, the remaining optical components of the microscope can be allowed to "float" relative to the objective lens with a looser-tolerance without degrading the operator's ability to align, observe, and optically direct an ophthalmic laser procedure.

3 Claims, 7 Drawing Sheets

SURGICAL LASER SYSTEM MICROSCOPE WITH SEPARATED OCULAR AND OBJECTIVE LENSES

BACKGROUND OF THE INVENTION

The present invention is generally related to microscope systems used to observe and/or direct laser eye surgery. In particular, the present invention provides devices, systems, and methods for structurally supporting the optical elements of a microscope relative to the optical train of the laser delivery system. The present invention is particularly useful for optically observing laser surgical procedures such as photo refractive keratectomy (PRK), photo therapeutic keratectomy (PTK), laser assisted in situ keratomileusis (LASIK), or the like.

Ophthalmic laser surgery and other ophthalmic procedures are often performed by a laser after optically aligning the laser with the eye using a microscope. While it may be possible to make use of lasers having other wavelengths, known laser eye surgery procedures generally include an ultra-violet or modified frequency infrared laser to remove a microscopic layer of stromal tissue from the eye's cornea to alter its refractive power. In one application, the laser removes a selected portion of this corneal tissue in order to correct refractive errors of the eyes. Laser ablation results in photo decomposition of the corneal tissue, but generally does not cause significant thermal damage to adjacent and underlying tissues of the eye. The irradiated molecules are broken into smaller volatile fragments photo chemically, directly breaking the intermolecular bonds. The microscope is often used to observe the treatment during and/or after the ablation, as well as to align the ablation with the eye.

Laser ablation procedures can remove the targeted stroma of the cornea to change the cornea's contour for varying purposes, such as for correcting myopia, hyperopia, astigmatism, and the like. While a variety of approaches and systems have been described for controlling the distribution of tissue ablation across the cornea, including masks, fixed and movable apertures, controlled scanning systems, eye movement tracking mechanisms, and the like, most laser eye systems include a microscope to aid the surgeon in aligning the patient's cornea with the laser system, and to allow the surgeon to optically monitor or verify that the targeted portion of the stroma is removed as intended.

Known laser eye surgery systems have generally included fairly standard microscope structures. The focus and field of view of a conventional microscope is often controlled by shifting the specimen to be viewed relative to the microscope structure. To target the field of view of microscopes used for laser eye surgery upon the patient's eye and allow observation of the laser beam delivery, these microscopes are instead often shifted in three dimensions relative to the support structure of the laser beam delivery system. Both positioning and stability of the microscope are tightly controlled, since any displacement of the microscope structure from proper alignment with the laser delivery location is magnified by the magnification of the microscope.

While these known laser eye surgery systems are quite effective, the cost and complexity of the microscope positioning and support structure are significant disadvantages. To provide adequate positioning and stability of the microscope relative to the laser delivery optical train, known laser eye surgery systems typically include a microscope adjustment structure having parts machined to tight tolerances. This adjustment structure often accommodates travel of the microscope in X, Y, and Z directions with a high degree of accuracy. These microscope adjustment mechanisms add significantly to the overall costs of the laser eye surgery system.

In light of the above, it would be desirable to provide improved laser eye surgery systems, devices, and methods. It would be particularly desirable to provide enhanced techniques for structurally supporting the microscope relative to the other components of the laser system. It would further be desirable if these improvements could be provided with less complexity, greater reliability, and a lower cost than known laser surgery/microscope support systems.

SUMMARY OF THE INVENTION

The present invention provides improved structures, systems, and methods for supporting the optical elements of a microscope relative to the optical train of a laser eye surgery system. The present invention generally takes advantage of a surprising characteristic of many microscopes: the field of view of the microscope can be substantially fully determined by the position of the objective lens. As a result, the field of view of the microscope can be fixed by accurately positioning just a portion of the many optical components of the microscope. In other words, the laser delivery optics and the microscope can be aligned with a target location of the patient's eye by accurately aligning just the objective lens with the delivery optics. By structurally separating the objective lens from the other optical components of the microscope, and by maintaining accurate alignment between the objective lens and the laser delivery optics with a simple, tight-tolerance support structure, the remaining optical components of the microscope can be allowed to "float" relative to the objective lens with a looser tolerance without degrading the operator's ability to align, observe, and optically direct a procedure, particularly when using a microscope having a Galilean magnification changer.

In a first aspect, the present invention provides a laser eye surgery system for resculpting a cornea of a patient. The system comprises a laser to produce a laser beam. Laser delivery optics are optically coupled to the laser so as to direct the laser beam toward the cornea of the patient. The laser directed by the laser delivery optics will generally alter refraction of the cornea. An optics support structure supports at least a portion of the delivery optics.

The laser eye surgery system further includes a microscope having an eyepiece, an objective lens, and a microscope body. The microscope body is attached to the optics support structure, and will directly support the eyepiece. Unconventionally, the laser optics support structure directly holds the objective lens in alignment with at least a portion of the delivery optics.

By supporting the objective lens and laser delivery optics with a common structural support system, the present invention can ensure alignment between the entire microscope and the treatment site. Advantageously, an off-the-shelf microscope can be modified for use in the present invention by removing its objective lens and mounting the microscope body and eyepiece on a mounting pad of the optic support structure. Even though the resulting positioning tolerance of the eyepiece of the microscope may be significantly looser than the positioning tolerance of the objective lens relative to the delivery optics, alignment is maintained between the field of view and treatment site. The laser beam will often be substantially coaxial with the objective lens, the objective lens often being disposed between the eyepiece of the microscope and a partially reflective mirror or other beam splitting structure. The off-the-shelf microscope will preferably comprise a binocular microscope having a Galilean magnification changer.

The optics support structure will generally restrain the objective lens of a microscope in fixed lateral alignment with a treatment axis of the laser beam. In production models, the objective lens will also be axially affixed relative to the treatment axis. Alternatively, particularly in pre-production development models of the present laser system, the axial position of the objective lens may be adjustable to determine the proper alignment between the field of view of the microscope and the laser delivery optics. Once this axial alignment has been determined, a variable axial positioner may be removed and replaced with a fixed spacer.

In another aspect, the present invention provides a method for fabricating a laser eye surgery system. The method comprises providing a microscope having an eyepiece supported relative to a mounting surface by a microscope body. An objective lens of the microscope, together with laser delivery optics, are mounted on a delivery optics support structure so that the optics support structure maintains alignment between the delivery optics and the objective lens with a first tolerance. The optics support structure includes a mounting pad, and the microscope body is attached to that mounting pad so as to align the eyepiece with the objective lens. The eyepiece is aligned with a second tolerance which is looser than the first tolerance.

Advantageously, the lateral alignment of the objective lens and a target axis of the delivery optics may be fixedly restrained by the optics support structure. An axial position of the objective lens may initially be determined using an adjustable positioner of the optic support structure. Once this axial position is determined, the adjustable positioner can be replaced with a fixed spacer to immovably restrain an objective lens at the determined axial position. This allows the field of view of the microscope to be permanently set at the desired position, and avoids having to resort to a complex, tight-tolerance, and expensive adjustment system for translating the microscope relative to the delivery optics in three dimensions. Fixing of the objective lens (and thereby the field of view of the microscope) also increases the efficiency of the system by eliminating the previously required steps of aligning the microscope with the targeted corneal tissues. Instead, the field of view of the microscope remains aligned with the treatment axis of the laser delivery optics when the cornea is positioned, generally by moving the entire patient on a moveable operating table.

DETAILED DESCRIPTION OF THE SPECIFIC EMBODIMENT

Figure 1:
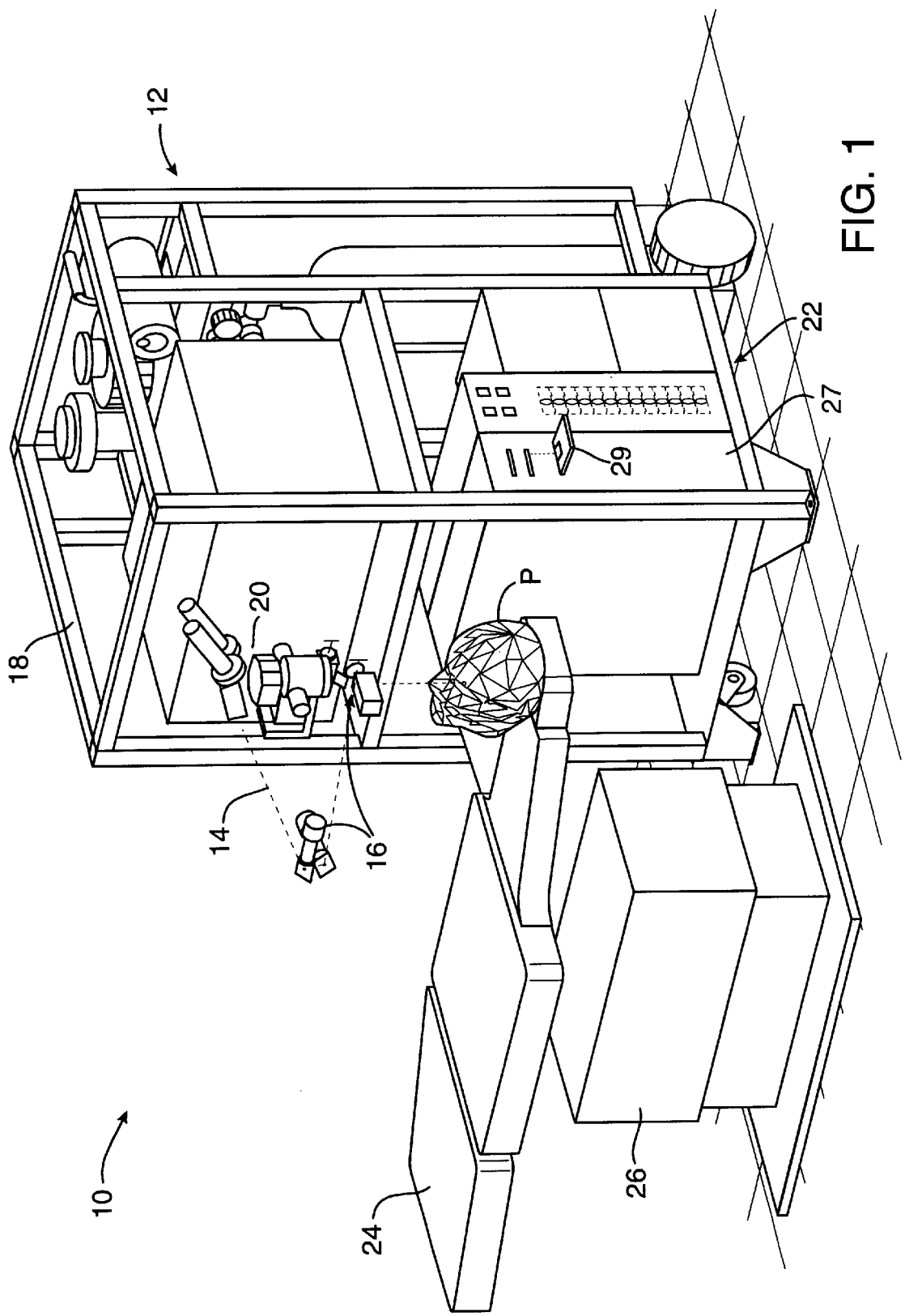
FIG. 1 is a perspective view of a laser eye surgery system according to the principles of the present invention, in which the structure supporting the microscope and laser delivery optics has been removed to more clearly show the optical components.

The present invention is generally directed to structures, systems, and methods for fabricating and supporting a microscope of a laser eye surgery system. The techniques of the present invention generally involve structurally separating the objective lens of the microscope from the microscope body. The separate objective lens is directly supported by the same structural frame work that holds the optical elements of the laser delivery system. The focus and field of view of a conventional microscope having a Galilean magnification changer is substantially determined by the position and orientation of the objective lens. As the desired field of view for a microscope used in laser eye surgery can be predetermined to allow observation of the delivery of the laser beam at the cornea, this allows the objective lens to be fixed in alignment with the laser delivery optics.

In general, positioning and stability of a microscope relative to the laser delivery system is very important. Any displacement of the microscope from the center of the laser delivery will be magnified by the microscope magnification setting in the image viewed through the microscope. To obtain the desired positioning and accuracy and stability, known laser eye surgery systems generally make use of expensive machined parts to allow displacement of the entire microscope in five degrees of freedom relative to the laser delivery site. By instead mounting the objective lens of the microscope to the support structure holding the laser delivery optics, the focus and field of view of the microscope can remain substantially aligned with the optical train for the laser beam. The positioning accuracy of the remaining optical components of the microscope can then be allowed to float with a looser tolerance in the X, Y, and Z directions. Despite minor variations in the positioning of the eyepiece (and other optical components of the microscope) relative to the objective lens, the focal plane and field of view of the microscope will remain aligned with the laser beam so long as the objective lens is firmly affixed relative to the laser delivery optics. Hence, the present invention effectively provides structural fixation of the microscope without having to provide all the complex and expensive microscope adjustment mechanisms generally found supporting the microscopes of laser eye surgery systems.

The present invention may find applications in a variety of settings. The invention generally allows alignment of a therapeutic or interventional laser beam with the field of view of a microscope, and may therefore be useful for a variety of laser surgeries, cellular manipulations, and the like. However, the most immediate application for the present invention will be in the field of laser eye surgery. As the structural system of the present invention maintains alignment between the microscope field of view and the laser delivery optics, the invention allows photoablation of selected portions of the cornea without having to realign the microscope and laser delivery optics for each procedure, daily, or at regular maintenance intervals. Hence, the present invention will have benefits for photo refractive keratectomy (PRK including procedures to correct hyperopia, myopia, astigmatism, or any combination thereof), photo therapeutic keratectomy (PTK), laser assisted in situ keratomileusis (LASIK), and the like.

Referring now to FIG. 1, a laser eye surgery system 10 includes a laser 12 that produces a laser beam 14. Laser 12 is optically coupled to laser delivery optics 16, which direct laser beam 14 to an eye of a patient P. A delivery optics support structure (see FIGS. 4–7, not shown here for clarity) extends from a frame 18 supporting laser 12. A microscope 20 is mounted on the delivery optic support structure.

Laser 12 generally comprise an excimer laser, ideally comprising an argon-fluorine laser producing pulses of laser light having a wavelength of approximately 193 nm. Laser 12 will preferably be designed to provide feedback stabilized fluence of 160 mJoules/cm$^2$ at the patient's eye, as delivered via delivery optics 16. The present invention may also be useful with alternative sources of radiation of any wavelength, particularly those adapted to controllably photodecompose the corneal tissue without causing significant damage to adjacent and/or underlying tissues of the eye.

Laser 12 and delivery optics 16 will generally direct laser beam 14 to the eye of patient P under the direction of a computer 22. Computer 22 will generally selectively expose portions of the cornea to laser pulses of laser beam 14 so as to effect resculpting of the cornea and alter the refractive characteristics of the eye.

Laser beam 14 may be tailored to produce the desired resculpting using one or more variable apertures (such as a variable iris and variable width slit as described in U.S. Pat. No. 5,713,892, the full disclosure of which is incorporated herein by reference), by varying the size and offset of the laser spot from the axis of the eye (as described in U.S. Pat. No. 5,683,379, and also described in co-pending U.S. patent application Ser. No. 08/968,380, filed Nov. 12, 1997, the full disclosures of which are incorporated herein by reference), by scanning the laser beam over the surface of the eye and controlling the number pulses and/or dwell time (as described by U.S. Pat. No. 4,665,913, the full disclosure of which is incorporated herein by reference), using masks in the optical path of laser beam 14 which ablate to varying the profile of the beam incident on the cornea (as described by U.S. patent application Ser. No. 08/468,895, filed Jun. 6, 1995, the full disclosure of which is incorporated herein by reference), or the like. The computer programs and control methodology for each of these resculpting techniques is well described in the patent literature.

Additional optical components may also be included in the optical path of laser beam 14, such as integrators to spatially and/or temporally control the distribution of energy within the laser beam (as described in U.S. Pat. No. 5,646,791, the disclosure of which is incorporated herein by reference), and the like. Similarly, other ancillary components of the laser surgery system which are not necessary to an understanding of the invention, such as an ablation effluent evacuator/filter, conventional computer sub-system components including the keyboard, the display, monitor, and program and data storage media, will often be provided, as should be understood by those of skill in the art.

The head of patient P will be firmly supported on, and preferably restrained by an operating table 24. Positioning of the eye relative to the laser delivery optics is generally effected by movement of the operating table 24. Hence, operating table 24 is supported by an actuation mechanism 26 which can move the patient to vertically and horizontally position the cornea of the eye at a predetermined target treatment site. Alternatively, microscope 20 and at least a portion of laser delivery optics 16 may move in unison to align laser beam 14 with the cornea. When the laser delivery optics are to be moved, the objective lens of microscope 20 will preferably remain affixed relative to at least a portion of the laser optical train adjacent the eye so as to maintain alignment between the microscope field of view and the laser treatment site.

Figure 2:
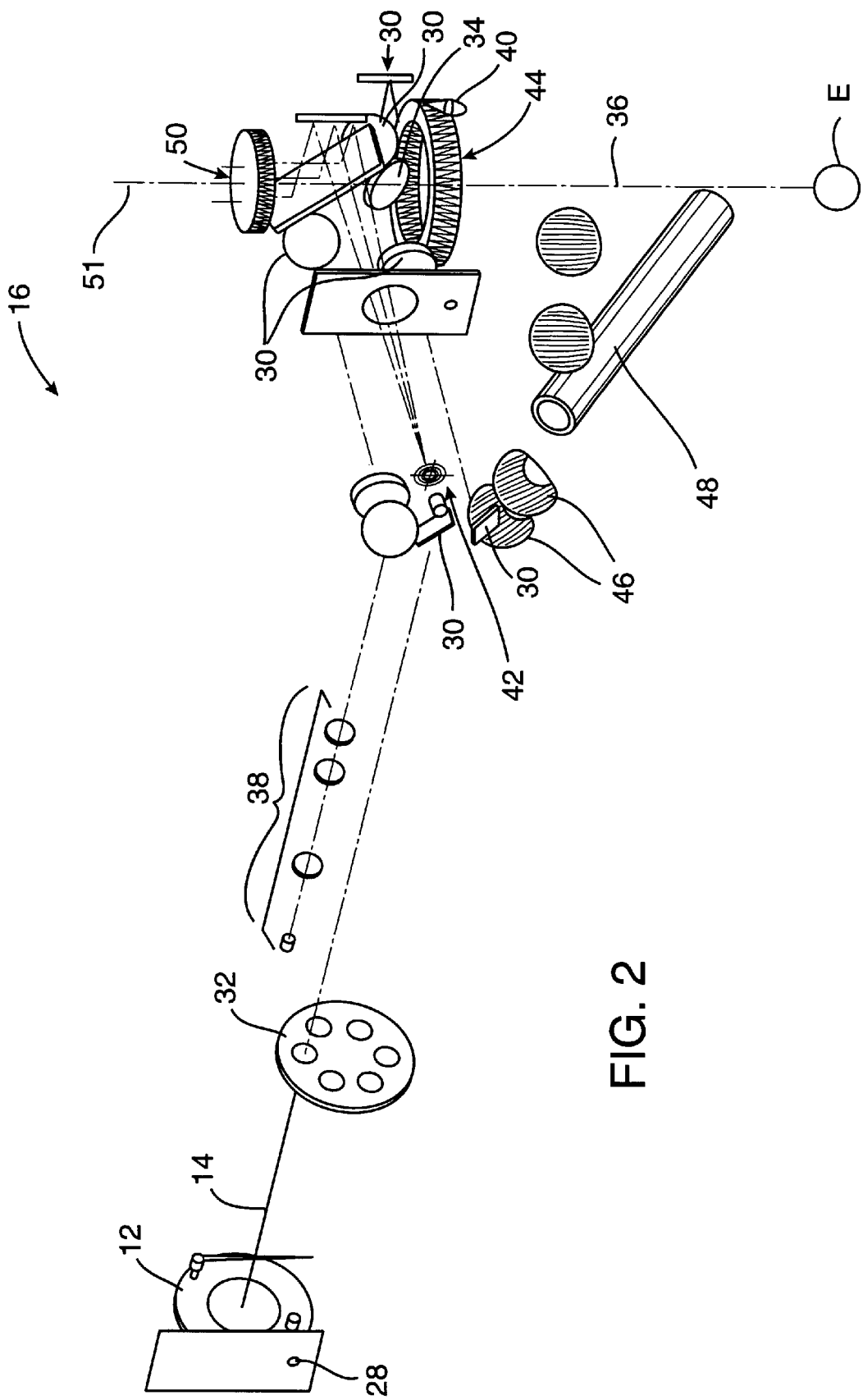
FIG. 2 is a perspective view of the laser delivery optics of another laser eye surgery system, including several of the optical sub-systems of the laser and the objective lens of the microscope.

Referring now to FIG. 2, several of the components of delivery optics 16 are illustrated with adjacent sub-systems of the laser delivery system. After passing a laser energy detector 28, laser beam 14 from laser 12 is directed through an aperture wheel 32. The laser beam then continues to a beam splitter 34 which directs laser beam 14 along a treatment axis 36 to eye E. To help the patient maintain eye E in the proper orientation, the patient will preferably maintain focus upon a target of patient fixation system 38. An alignment system 40 helps the laser system operator properly position the patient for treatment. A reticle 42 can be projected into the microscope as shown. Illumination of the eye can be provided using a ring illuminator 44 and oblique illuminators 46, while aspiration of photo decomposition debris can be provided by aspiration nozzle 48. It should be noted that the specific arrangement of optical elements and support structure of the illustrated laser eye surgery systems may vary somewhat between the figures.

Of particular importance for the present invention, an objective lens 50 of microscope 20 (see FIG. 1) is disposed in close proximity to the downstream elements of laser delivery optics 16. Objective lens 50 will preferably have an axis 51 coaxially aligned with treatment axis 36. Beam splitter 34, which will typically be in the form of a partially reflective mirror so as to redirect laser beam 14, will transmit visible light provided by obliques 46 and ring illuminator 44 as scattered by eye E to the objective lens, so that the eye can be imaged without having to transmit the high powered laser beam through the objective lens of the microscope.

Figure 3:
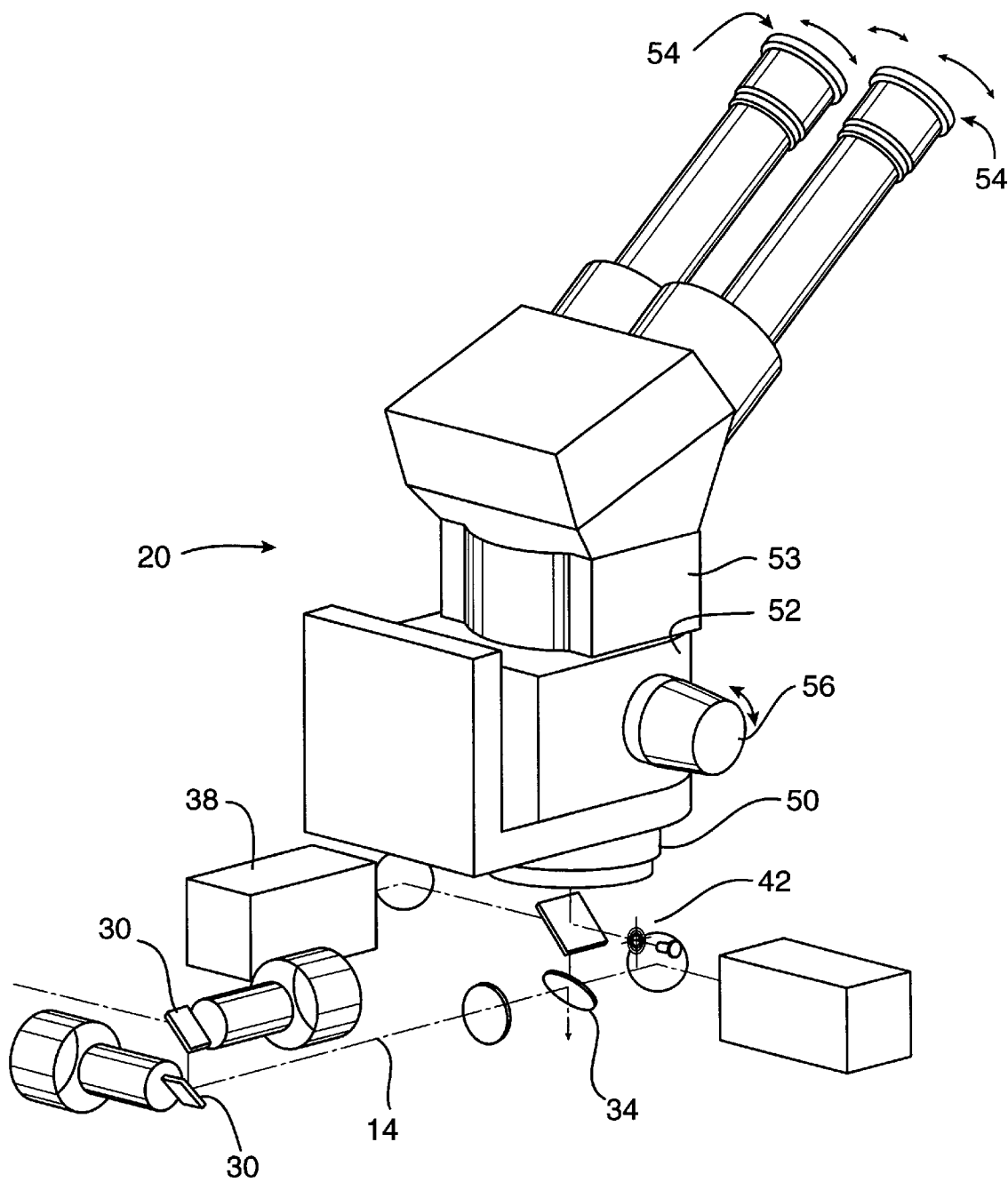
FIG. 3 is a perspective view of a microscope together with and some of the laser delivery optics.

The arrangement of the optical components of delivery optics 16 adjacent microscope 20 is seen most clearly in FIG. 3. Mirrors 30 are adjustably mounted to allow alignment of laser beam 14 relative to the treatment pattern. Microscope 20 makes use of, but is largely structurally separated from objective lens 50. Along with objective lens 50, microscope 20 also includes a microscope body 52 and a pair of binocular eye pieces 54. An optical beam splitter 53 is disposed between body 52 and eye pieces 54 to allow a video system to be coupled to the microscope so that assistants may observe the procedure and the like.

Microscope body 52 supports a Galilean magnification changer 56. Such Galilean magnification changers typically allow incremental adjustment of the magnification of the microscope by moving one or more lens sets into or out of the optical path between objective lens 50 and eye pieces 54 so as to alternatively increase, decrease, or have no effect on the magnification provided by the microscope.

Microscopes having Galilean magnification changers are commercially available from Leica of Switzerland; from Zeiss of Germany; and others. In general, these commercially available microscopes are provided with an integral objective lens supported directly by the microscope body. Such off-the-shelf microscopes may be modified for use according to the present invention by removing the objective lens, they may be ordered from the supplier without the objective lens, or they may be specially fabricated for use in the present laser system, all within the scope of the present invention. In general, these microscopes provide three or five magnification settings as determined by rotating magnification changer 56. Adjustments are often provided so as to accommodate a few diopters of myopia or hyperopia in each eye of the person viewing the laser eye surgery procedure through the microscope. The optical components of microscope 20 are illustrated in FIG. 4, and a particularly preferred microscope for modification and use within the present laser eye surgery system is commercially available from Leica of Heerbrugg, Switzerland under Model No. MS5.

Figure 4:
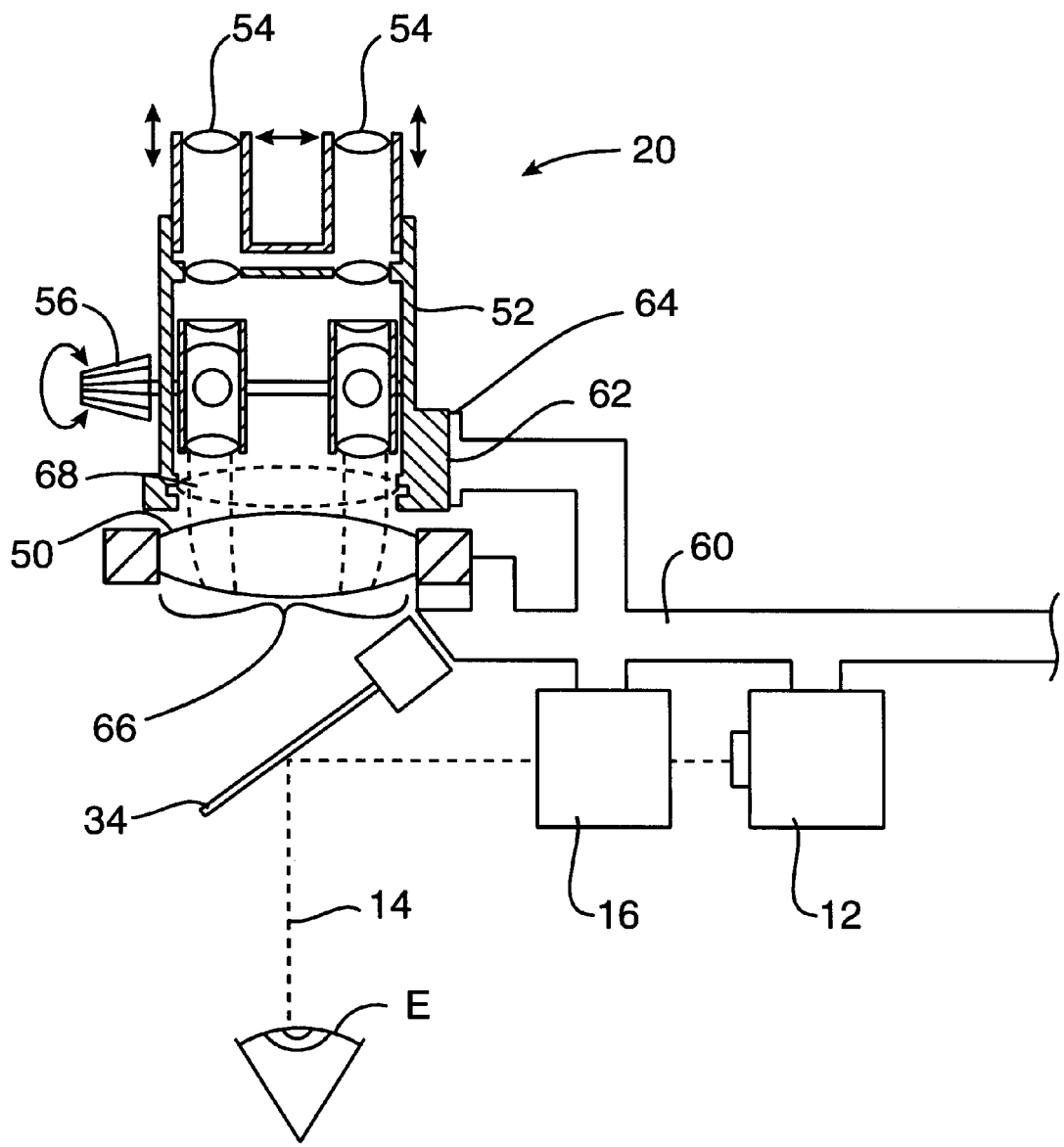
FIG. 4 is a schematic illustration showing how the optics support structure maintains a fixed alignment between the objective lens and laser delivery optics, and also illustrates how the remaining components of the microscope are allowed to float at a looser tolerance.

The structural support arrangement of the present invention can be understood most easily with reference to FIG. 4. Delivery optics 16 (including beam splitter 34) are held in alignment with eye E by a delivery optics support structure 60. To maintain alignment between the eye and the field of view of microscope 20, objective lens 50 is also directly supported by delivery optics support structure 60. Eye pieces 54 (and the other optical components of microscope 20) are supported by microscope body 52 in a conventional manner. To maintain alignment between eye pieces 54 and objective lens 50, microscope body 52 includes a mounting surface 62 which engages a mounting pad 64 of delivery optics support structure 60.

As objective lens 50 is directly mounted to delivery optics support structure 60, alignment between the objective lens and laser delivery optics 16 (and hence to laser beam 14) can be maintained to a very tight tolerance. Preferably, objective lens 50 is positioned relative to delivery optics 16 within a tolerance of about 0.5 mm or more, the objective lens ideally being positioned relative to the delivery optics within a tolerance of 0.2 mm.

As described above, the accurate positioning of objective lens 50 relative to laser delivery optics 16 ensures that the field of view of microscope 20 will be properly positioned relative to the corneal treatment site. As a result, the other optical components of microscope 20 (including eye pieces 54) can be allowed to float in the X, Y, and Z directions with a relatively loose tolerance support structure. Hence, eye pieces 54 may be supported by microscope body 52, mounting surface 62, mounting pad 64, and delivery optics support structure 60 with a tolerance of about ±2.5 mm relative to objective lens 50. The total lateral tolerance, or X and Y displacement, of the optical components supported by microscope body 52 relative to the corneal treatment site on eye E will actually be determined by the characteristics of objective lens 50. More specifically, a high quality image of the corneal treatment site can be provided through microscope 20 so long as objective lens 50 is aligned laterally with the treatment axis, and so long as the other optical components of microscope 20 remain aligned within a distortion-free zone 66 of objective lens 50. Hence, allowable lateral displacement of these optical components can be enhanced by providing an objective lens which has a distortion-free zone that is significantly larger than would be required if objective lens 50 were affixed directly to the microscope body. In the exemplary embodiment, objective lens 50 comprises a 50.0 mm diameter lens having a focal length of 300 mm, the objective lens being formed of two adjacent lenses and coated with a broadband anti-reflective coating.

Figure 5:
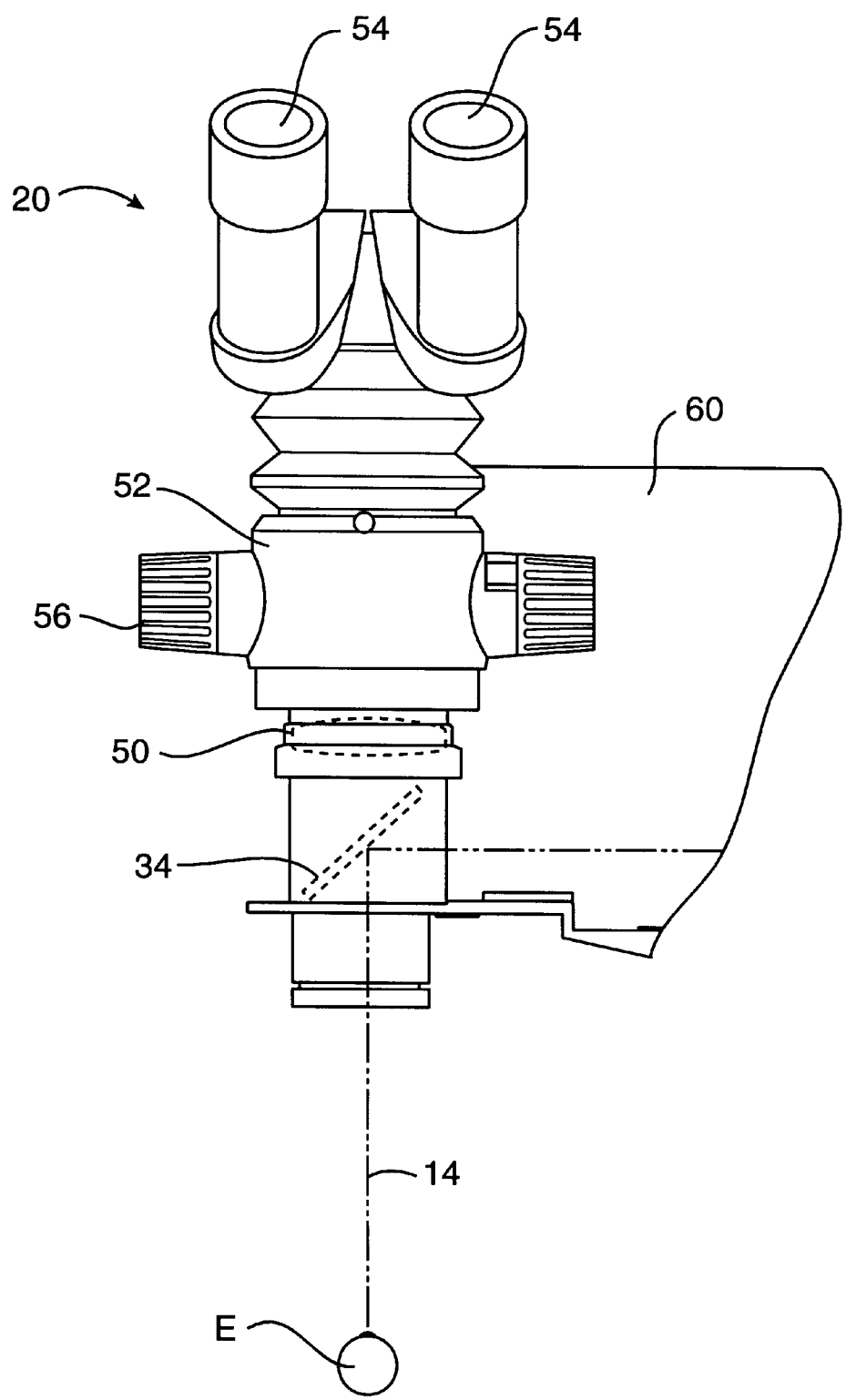
FIG. 5 is a front view of a microscope showing a portion of the laser delivery optics of another laser eye surgery system.
Figure 6:
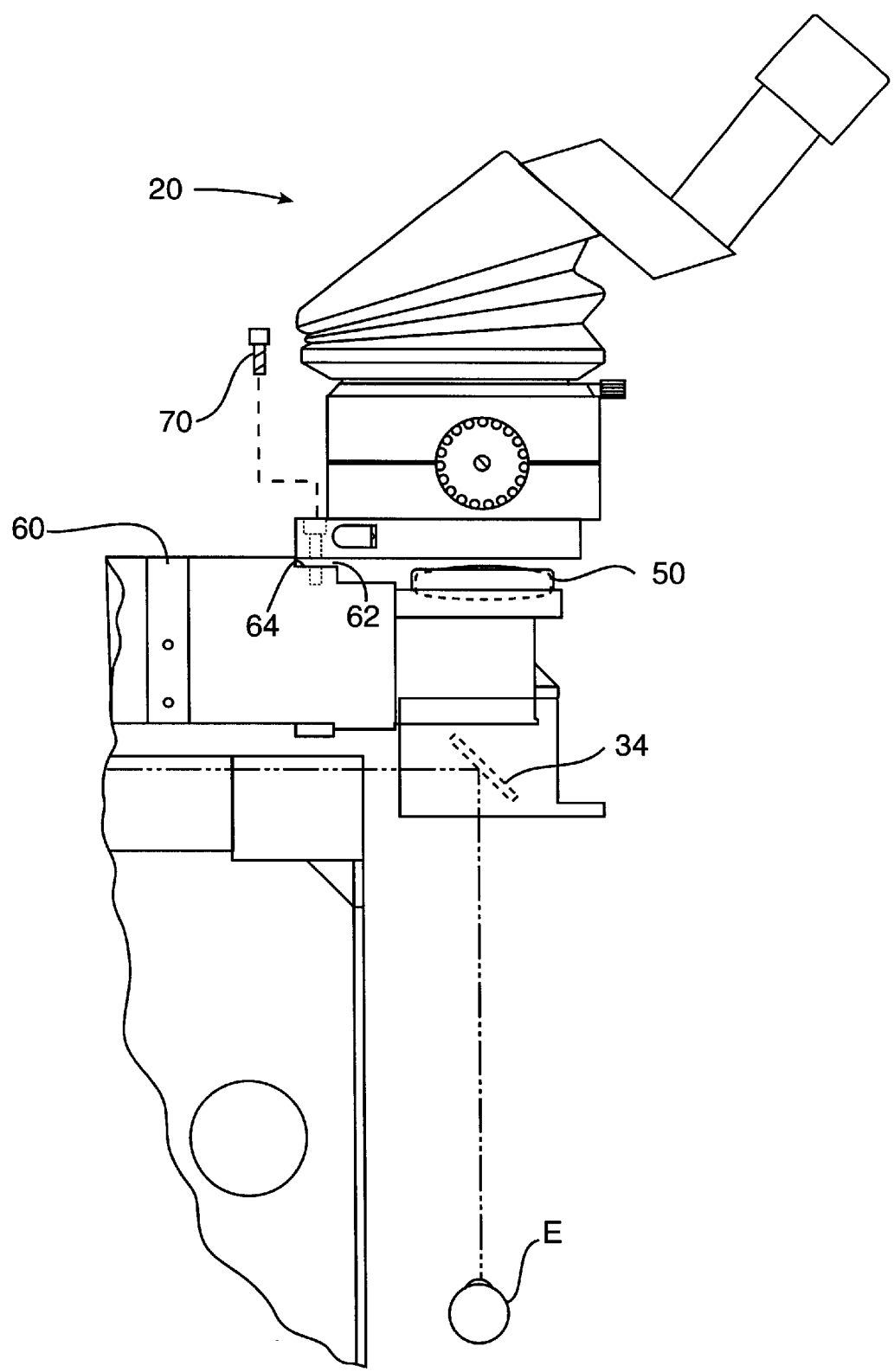
FIG. 6 is an exploded side view of the microscope body and optic support structure.
Figure 7:
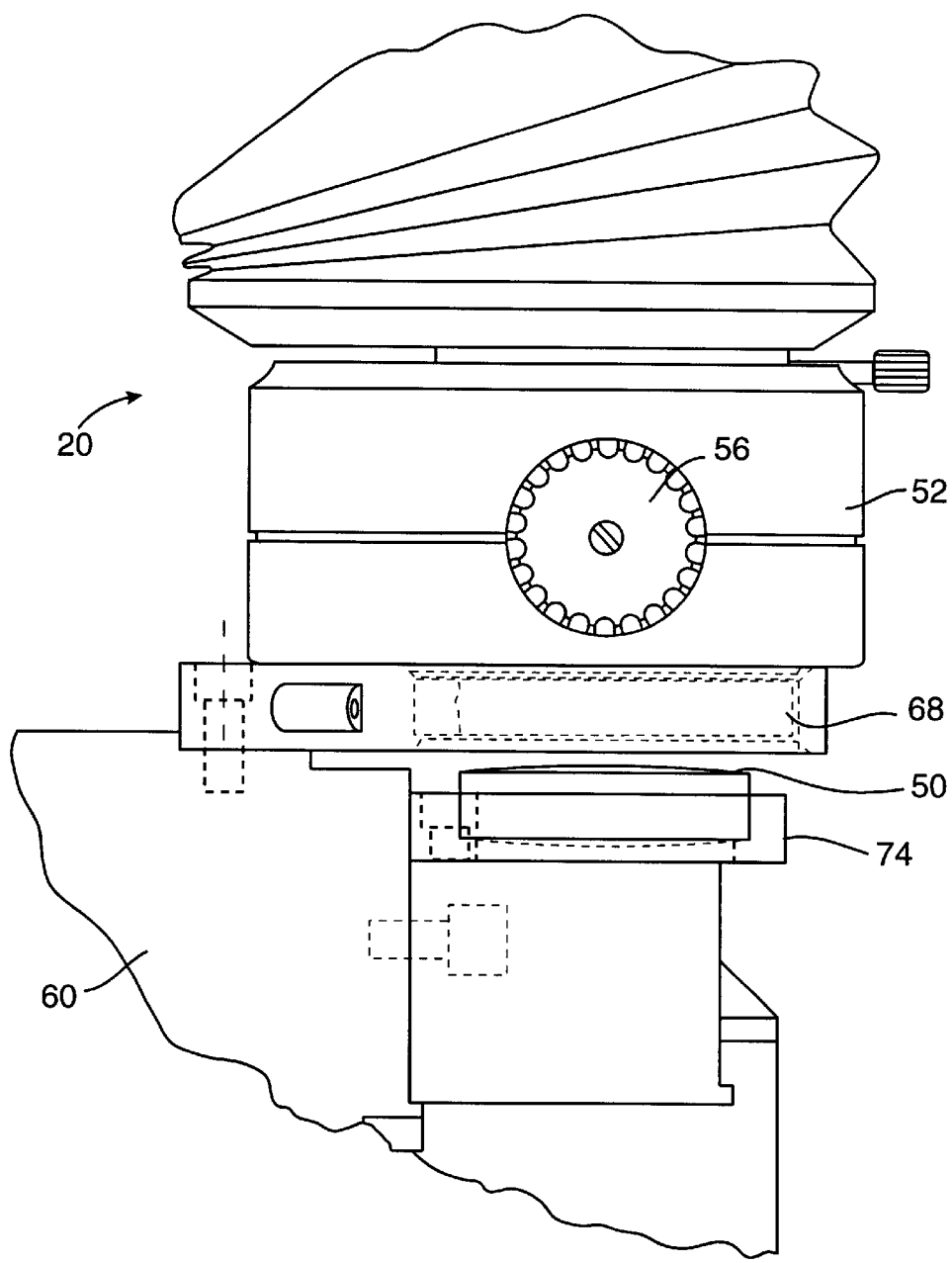
FIG. 7 is a detailed view showing the mounting of the microscope body to the optics support structure, and also illustrating a fixed spacer which axially positions the objective lens.

An exemplary structural interface between microscope 20 and delivery optics support structures 60 is illustrated in more detail in FIGS. 5–7. Rather than occupying the standard position 68 for an objective lens affixed directly to microscope body 52, objective lens 50 is fastened to delivery optics support structure 60 as shown. After removal of its standard objective lens, microscope 20 is mounted to delivery optics support structure 60 by fastening mounting surface 62 of the microscope to mounting pad 64 of the support structure with fasteners 70.

Figure 8:
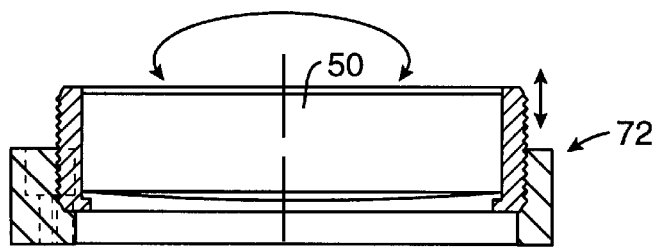
FIG. 8 is a cross-sectional view of an adjustable positioner to determine the desired axial position of the objective lens prior to fabricating the fixed spacer of FIG. 7.

Although it is possible to accurately determine the proper lateral position of objective lens 50 prior to fabrication of delivery optics support structure 60 and assembly of the microscope and support structure together, calculation of the axial position of the objective lens relative to the corneal treatment site is somewhat more problematic. Empirical calculations of the focal plane of the image viewed through microscope 20 can be somewhat misleading, so that the desired position for objective lens 50 may benefit from slight adjustments from those calculated. Nonetheless, once the proper axial position has been determined, reliable focal plain positioning should be possible by repeating the lessons learned during development. Therefore, the present invention provides a variable axial positioner 72 as illustrated in FIG. 8.

Objective lens 50 can be axially positioned using variable positioner 72 by affixing the variable positioner to delivery optics support structure 60 in place of a fixed spacer 74. This allows adjustment to the axial position of the objective lens 50 within the assembled microscope and laser system. Once the proper axial position is determined, the dimensions of fixed spacer 74 can be set. Production versions of the laser system will then include fixed spacer 74 affixed to delivery optics support structure 60 as shown in FIGS. 6 and 7. As a result of this development process, the focal plain of microscope 20 should be immediately and repeatably positioned at the corneal treatment site upon assembly of the surgery system, without requiring translation and adjustment of the entire microscope structure.

While the exemplary embodiment of the present invention has been described in some detail, by way of example and clarity of understanding, a variety of modifications, adaptations, and changes will be obvious to those of skill in the art. For example, the present invention may be used with microscopes having a single ocular lens rather than the binocular structures illustrated and described herein. Additionally, the beam splitter may redirect the optical image while transmitting the laser beam, or may be pivotally mounted to scan the laser beam across the cornea about the treatment axis. Hence, the scope of the present invention is limited solely by the appended claims.

What is claimed is:

1. A method for fabricating a laser eye surgery system, the method comprising;

providing a microscope having an eyepiece supported relative to a mounting surface by a microscope body;

mounting an objective lens of the microscope and laser delivery optics on a delivery optics support structure so that the optics support structure maintains alignment between the delivery optics and the objective lens with a first tolerance, the optics support structure having a mounting pad;

attaching the microscope body to the mounting pad of the optics support structure so as to align the eyepiece with the objective lens with a second tolerance which is looser than the first tolerance.

2. The laser system fabrication method of claim 1, further comprising fixedly restraining lateral alignment of the objective lens with a target axis of the delivery optics with the optics support structure.

3. The laser system fabrication method of claim 2, further comprising determining an axial position of the objective lens using an adjustable positioner of the optics support structure, and replacing the adjustable positioner with a fixed spacer, the fixed spacer immovably restraining axial alignment of the objective lens at the determined position.

* * * * *